US008359721B2

(12) United States Patent
Melsheimer et al.

(10) Patent No.: US 8,359,721 B2
(45) Date of Patent: Jan. 29, 2013

(54) SLIDING SPLIT-SLEEVE IMPLANT COMPRESSOR

(75) Inventors: Jeffry S. Melsheimer, Springville, IN (US); Grant T. Hoffman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1180 days.

(21) Appl. No.: 12/204,376

(22) Filed: Sep. 4, 2008

(65) Prior Publication Data

US 2010/0057185 A1 Mar. 4, 2010

(51) Int. Cl.
*B23P 19/04* (2006.01)
*B23P 19/02* (2006.01)
*A61F 11/00* (2006.01)
*A61F 2/06* (2006.01)
*A61M 29/00* (2006.01)

(52) U.S. Cl. ............. 29/238; 29/235; 29/239; 606/198; 606/108; 623/1.11

(58) Field of Classification Search ................... 29/238, 29/235, 239; 606/198, 194, 108; 623/1, 623/1.11, 1.12
See application file for complete search history.

(56) References Cited

U.S. PATENT DOCUMENTS

| | | | | |
|---|---|---|---|---|
| 5,026,377 A | * | 6/1991 | Burton et al. | 606/108 |
| 5,630,830 A | | 5/1997 | Verbeek | 606/198 |
| 5,672,169 A | * | 9/1997 | Verbeek | 606/1 |
| 5,709,703 A | | 1/1998 | Lukic et al. | 606/198 |
| 5,746,764 A | | 5/1998 | Green et al. | 606/194 |
| 5,783,227 A | * | 7/1998 | Dunham | 425/318 |
| 6,004,328 A | | 12/1999 | Solar | 606/108 |
| 6,068,635 A | * | 5/2000 | Gianotti | 29/235 |
| 6,090,035 A | * | 7/2000 | Campbell et al. | 600/7 |
| 6,092,273 A | * | 7/2000 | Villareal | 29/516 |
| 6,110,198 A | | 8/2000 | Fogarty et al. | 623/1.12 |
| 6,126,685 A | | 10/2000 | Lenker et al. | 623/1 |
| 6,132,458 A | | 10/2000 | Staehle et al. | 623/1.11 |
| 6,149,680 A | * | 11/2000 | Shelso et al. | 623/1.11 |
| 6,162,244 A | | 12/2000 | Braun et al. | 623/1.12 |
| 6,167,605 B1 | | 1/2001 | Morales | 29/282 |
| 6,471,718 B1 | | 10/2002 | Staehle et al. | 623/1.11 |
| 6,514,280 B1 | * | 2/2003 | Gilson | 623/1.11 |
| 6,618,921 B1 | * | 9/2003 | Thornton | 29/270 |
| 6,902,575 B2 | * | 6/2005 | Laakso et al. | 623/1.11 |

(Continued)

FOREIGN PATENT DOCUMENTS

EP 607468 A1 * 7/1994

*Primary Examiner* — Lee D Wilson
*Assistant Examiner* — Alvin Grant
(74) *Attorney, Agent, or Firm* — Brinks Hofer Gilson & Lione

(57) ABSTRACT

A system and method for loading an endoprosthesis, such as a stent or valve, into an introducer is provided that permits interventionalists to load the endoprosthesis easily at the bedside. The system can include a compressor for compressing the endoprosthesis to a cross-sectional area less than the cross-sectional area of the introducer lumen. The compressor has a funnel portion at one end where the un-compressed endoprosthesis can be introduced and another end where the introducer and sleeves of a split sleeve device are inserted. The sleeves conform to the compressor passage and surround the endoprosthesis to collapse the endoprosthesis. The split sleeve device also includes a mounting device coupled to the sleeves. The endoprosthesis is compressed and loaded into the introducer by the relative movement of the mounting device and the compressor, where the endoprosthesis remains generally stationary while being compressed and loaded in order to avoid potentially compromising the endoprosthesis.

20 Claims, 4 Drawing Sheets

U.S. PATENT DOCUMENTS

| | | | |
|---|---|---|---|
| 6,920,674 B2 * | 7/2005 | Thornton | 29/270 |
| 6,926,732 B2 * | 8/2005 | Derus et al. | 623/1.12 |
| 7,127,789 B2 * | 10/2006 | Stinson | 29/434 |
| 7,691,109 B2 * | 4/2010 | Armstrong et al. | 606/108 |
| 7,717,934 B2 * | 5/2010 | Kusleika | 606/200 |
| 8,006,535 B2 * | 8/2011 | Righini et al. | 72/402 |
| 8,112,857 B2 * | 2/2012 | Voelkl | 29/243.5 |
| 2003/0083730 A1 | 5/2003 | Stinson | 623/1.11 |
| 2003/0114910 A1 * | 6/2003 | Juhani Laakso et al. | 623/1.11 |
| 2003/0236545 A1 * | 12/2003 | Gilson | 606/191 |
| 2004/0015224 A1 * | 1/2004 | Armstrong et al. | 623/1.12 |
| 2006/0052750 A1 * | 3/2006 | Lenker et al. | 604/164.01 |
| 2006/0190071 A1 * | 8/2006 | Armstrong et al. | 623/1.12 |
| 2007/0118207 A1 * | 5/2007 | Amplatz et al. | 623/1.12 |
| 2007/0198077 A1 * | 8/2007 | Cully et al. | 623/1.12 |
| 2007/0270932 A1 * | 11/2007 | Headley et al. | 623/1.11 |
| 2008/0119890 A1 * | 5/2008 | Adams et al. | 606/200 |
| 2008/0188888 A1 * | 8/2008 | Adams et al. | 606/200 |
| 2009/0076587 A1 * | 3/2009 | Cully et al. | 623/1.13 |
| 2009/0248142 A1 * | 10/2009 | Perkins et al. | 623/1.24 |
| 2010/0179491 A1 * | 7/2010 | Adams et al. | 604/264 |
| 2010/0331956 A1 * | 12/2010 | Armstrong et al. | 623/1.12 |
| 2011/0015714 A1 * | 1/2011 | Atkinson et al. | 607/126 |
| 2011/0221113 A1 * | 9/2011 | Diederichs | 269/20 |
| 2011/0258833 A1 * | 10/2011 | Austin | 29/516 |
| 2011/0301703 A1 * | 12/2011 | Glazier | 623/2.17 |

* cited by examiner

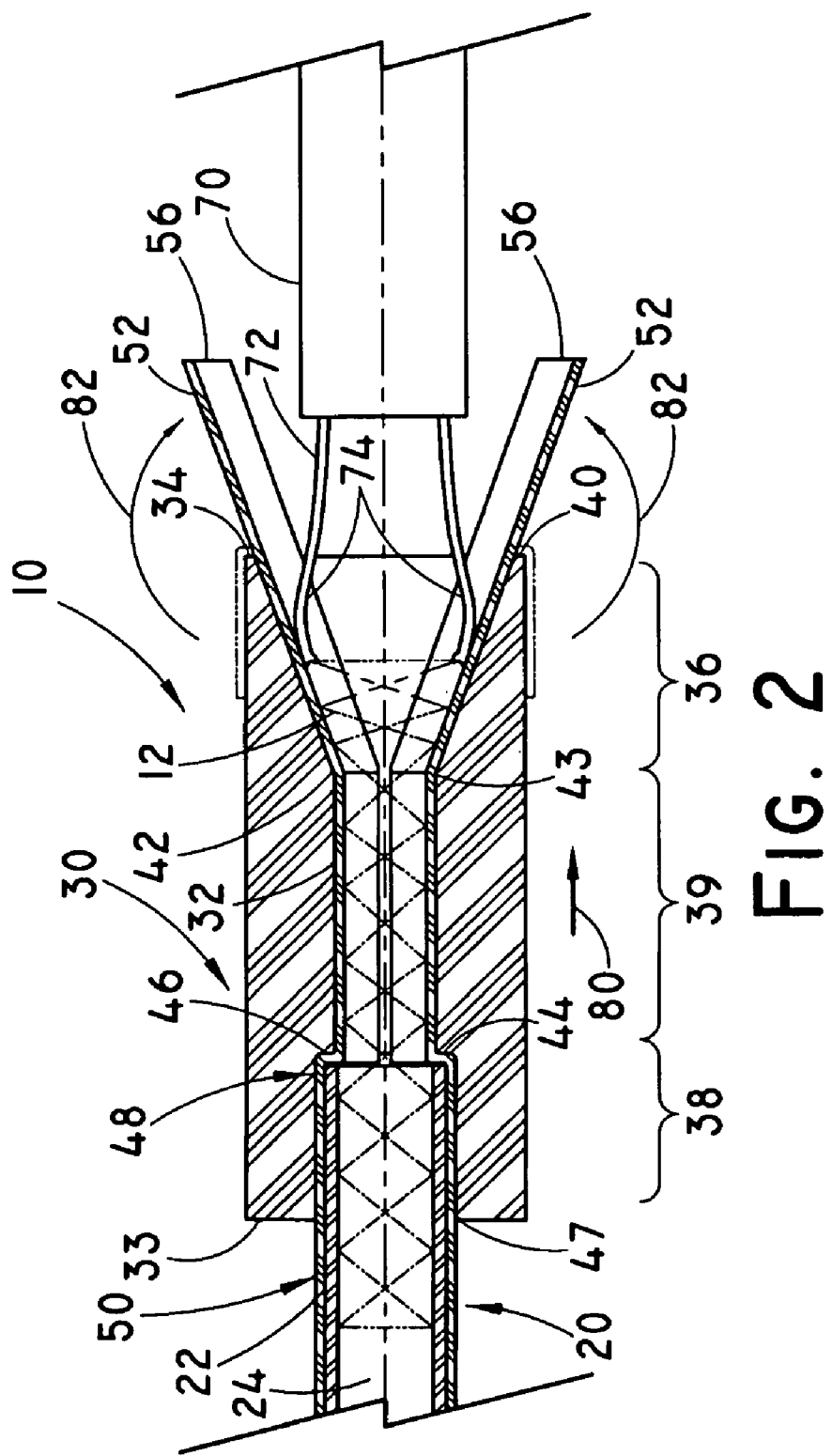

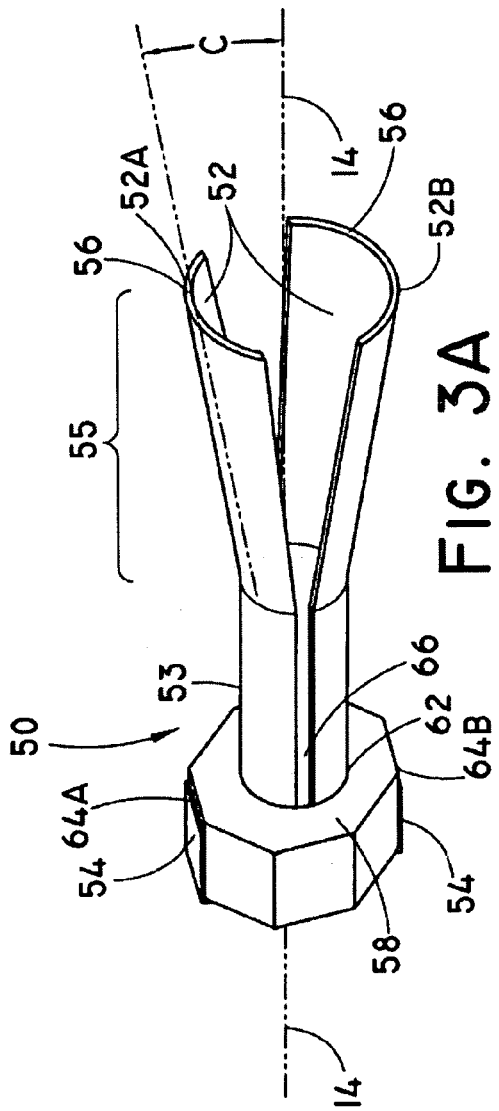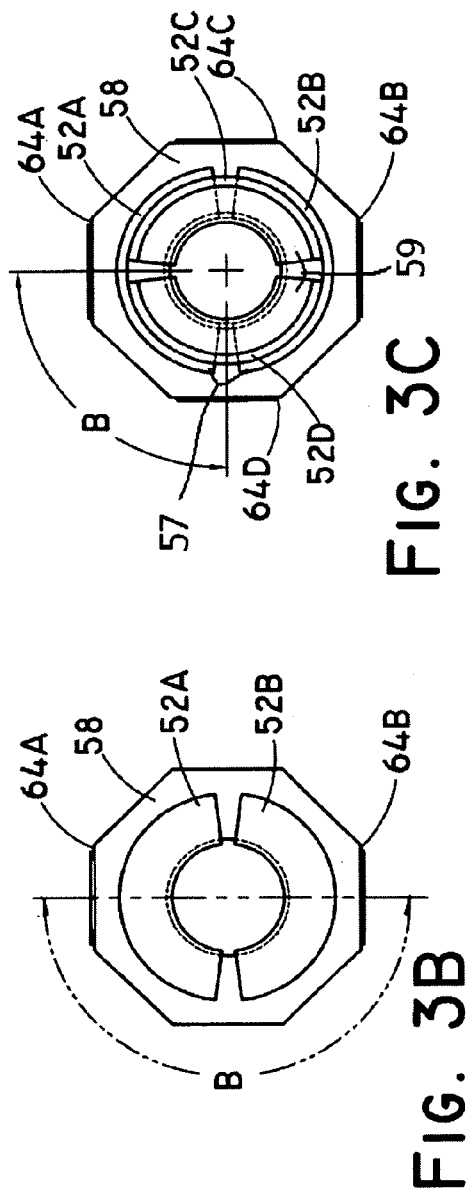

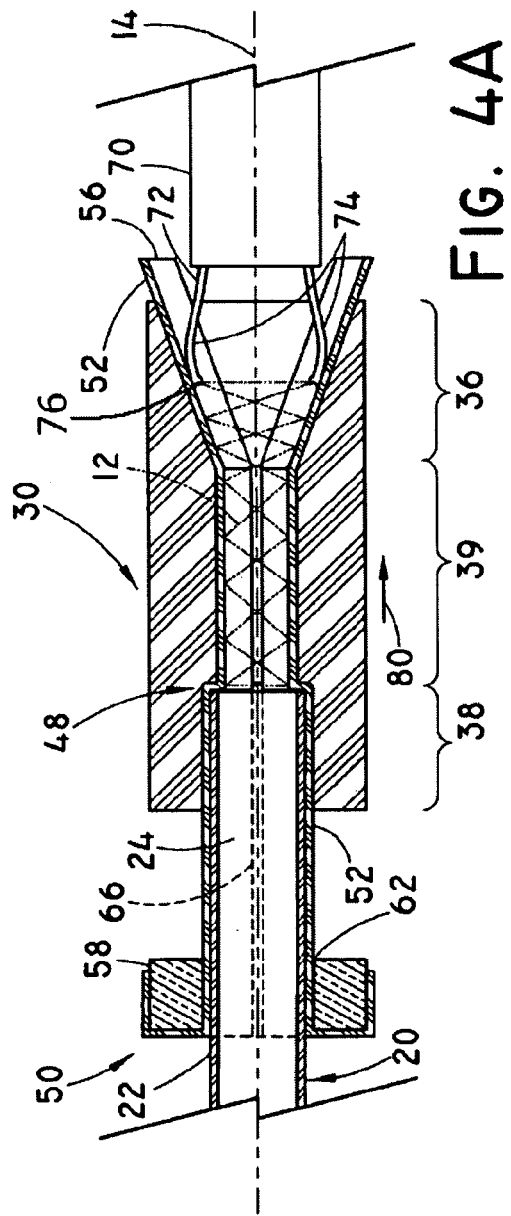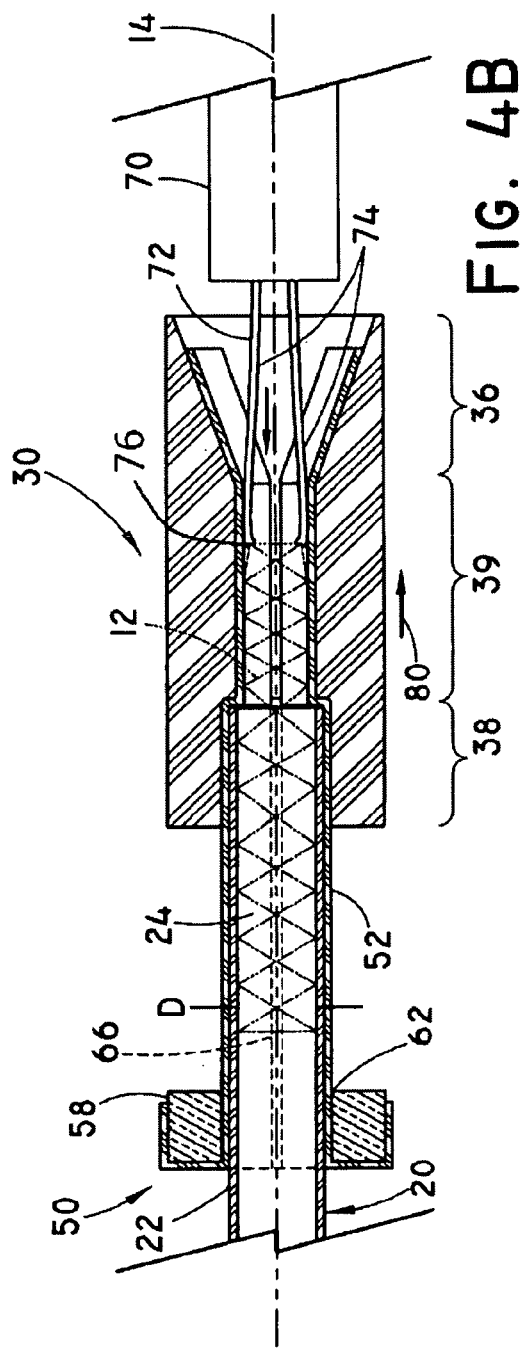

SLIDING SPLIT-SLEEVE IMPLANT COMPRESSOR

BACKGROUND

1. Field of the Invention

This invention generally relates to systems for loading medical devices into deployment devices, and particularly to a system comprising an expandable medical device, a deployment device, and a loading device which loads the expandable medical device into the deployment device.

2. Background of the Invention

Stents and valves are known endoprostheses. Endoprostheses are generally radially-expandable, tubular structures that are configured to be delivered to a body vessel to support or repair the body vessel. During delivery of the endoprosthesis, the endoprosthesis remains in a radially compressed configuration in a deployment device. When the endoprosthesis is delivered to a treatment site within the body vessel, the endoprosthesis is then released from the deployment device, and expands to implant onto the body vessel wall.

Deployment devices are typically tubular device including an outer cross-sectional area that is sized to navigate through the body vessels or through the working channels of an endoscope or the like to the treatment site. Endoprosthesis, therefore, must be radially compressed to a cross sectional area in order to be loaded into the lumen of the deployment device via a compressing device, which commonly occurs at the manufacturing and/or assembly site. Some compressing devices may push the endoprosthesis through a funnel to radially compress the endoprosthesis to load into the delivery device, while other compressing devices may diminish the cross-sectional area of the endoprosthesis and then push the endoprosthesis into the catheter. These methods and systems have shortcomings for at least two reasons. First, pushing an uncompressed endoprosthesis into a funnel may fail due to insufficient column strength. Second, pushing a compressed endoprosthesis along the surface of the compressing device may fail due to wall friction. Regardless, the endoprosthesis may be compromised while pushing the endoprosthesis through the compressing device, compromising the drug coating, graft and/or valve material, and/or barbs.

Nevertheless, in the event that a vascular condition may be treated by virtue of the replacement endoprosthesis, the need arises to compress the aforementioned endoprosthesis for delivery. Some endoprostheses, however, need to remain uncompressed up until the time of delivery. For example, an endoprosthesis with remodelable material may need to remain hydrated and uncompressed until delivery into the body. In the alternative, an endoprosthesis may be packaged separately from the deployment device. Such medical devices, nonetheless, must then be compressed into the deployment device at the bedside by the interventionalist. Thus, there remains a need for an apparatus and/or system to compress and load an endoprosthesis into a deployment device. There further remains a need to compress the endoprosthesis without compromising the drug coating, graft and/or valve material, and/or barbs, if present.

SUMMARY

A system and method for loading a tubular medical device into an introducer having an outer tube defining a lumen are provided. The system can include components that can be individually packaged and sterilized. The interventionalist, consequently, can load the tubular medical device at the bedside of a patient. Further, the components of the system are preferably disposable after one-time use, or alternatively can be made of materials that can be cleaned, reset, sterilized and reused.

The system can include a compressor having a stent delivery end, a stent receiving end, and a passage about a longitudinal axis connecting the stent delivery end and the stent receiving end. The passage can include a funnel portion proximate the stent receiving end and an introducer opening proximate the stent delivery end. The funnel portion at the stent receiving end can be sized to receive an un-compressed stent. The introducer opening can be shaped and sized to receive the outer tube of the introducer.

The funnel portion of the compressor passage can have a first end corresponding to the stent receiving end and a second end. The first end of the funnel portion can be sized to receive said tubular medical device in the expanded configuration. The second end can have a cross-sectional area substantially the same or less than a cross-sectional area of the lumen of the introducer. A transitioning portion can be interposed between the funnel portion and the introducer opening. The transitioning portion can have a cross-sectional area substantially the same or less than the cross-sectional area of the lumen of the introducer. The compressor passage can also include a seat for the introducer within the introducer opening. The seat can be sized to prevent said introducer from advancing into the funnel portion.

The system can also include a split sleeve device including at least one flexible sleeve and a mounting device. The sleeves can have a first end and a second end. The mounting device can be situated adjacent the stent delivery end of the compressor and can define a hole about the longitudinal axis. The hole can be sized to surround the outer tube of the introducer. The first end of the sleeves can be coupled to the mounting device, while the second end of the sleeves can extend through the compressor passage at least to the stent receiving end. The second end of sleeves can further be flared outward to surround the un-compressed tubular medical device. The mounting device can be movable away from the compressor with the first end of the at least one flexible sleeve, drawing the second end of the at least one flexible sleeve and surrounded tubular medical device through the funnel portion to collapse the tubular medical device to a compressed configuration. The compressed tubular medical device can be urged into the lumen of the introducer by the movement of the flexible sleeves relative to the compressor and the introducer.

The system may further include an inserter having a collapsible member configured to retain the tubular medical device about the longitudinal axis while the tubular medical device collapses to the compressed configuration and is loaded into the lumen of the introducer. The collapsible member of the inserter can include a plurality of arms extending radially outward from the inserter. Each arm can have a stent engaging end to retain the tubular medical device about the longitudinal axis while the tubular medical device collapses to the compressed configuration. The collapsible member can be collapsible to a cross-sectional area less than the cross-sectional area of the introducer lumen. The collapsible member may be configured to be inserted into the lumen of the introducer when urging tubular medical device into the lumen of the introducer.

One of the advantages of the system and method provided is that the tubular medical device remains generally stationary while being compressed by the sleeves. Consequently, the system and method can avoid compromising a drug coating, graft, valve, or anchoring means of the tubular medical device by avoiding sliding contact between the walls of the compressing device and the tubular medical device.

The above, as well as other advantages of the present invention, will become readily apparent to those skilled in the art from the following detailed description of a preferred embodiment when considered in the light of the accompanying drawings.

BRIEF DESCRIPTION OF THE DRAWINGS

FIG. 2 is a cross-sectional view of an exemplary system of the present invention, including a tubular medical device, an introducer, a compressor, a portion of a split sleeve device, and an inserter.

FIG. 3A is a perspective view of a split sleeve device.

FIG. 3B is an end view of the split sleeve device of FIG. 3A.

FIG. 3C is a view similar to FIG. 3B illustrating four sleeves.

FIG. 4A is a side view of an exemplary system of the present invention illustrating the loading of a tubular medical device into a compressor and a split sleeve device.

FIG. 4B is a side view of the system of FIG. 4A illustrating the loading of the tubular medical device into an introducer via the compressor and the split sleeve device.

DESCRIPTION OF PREFERRED EMBODIMENTS

Figure 1:
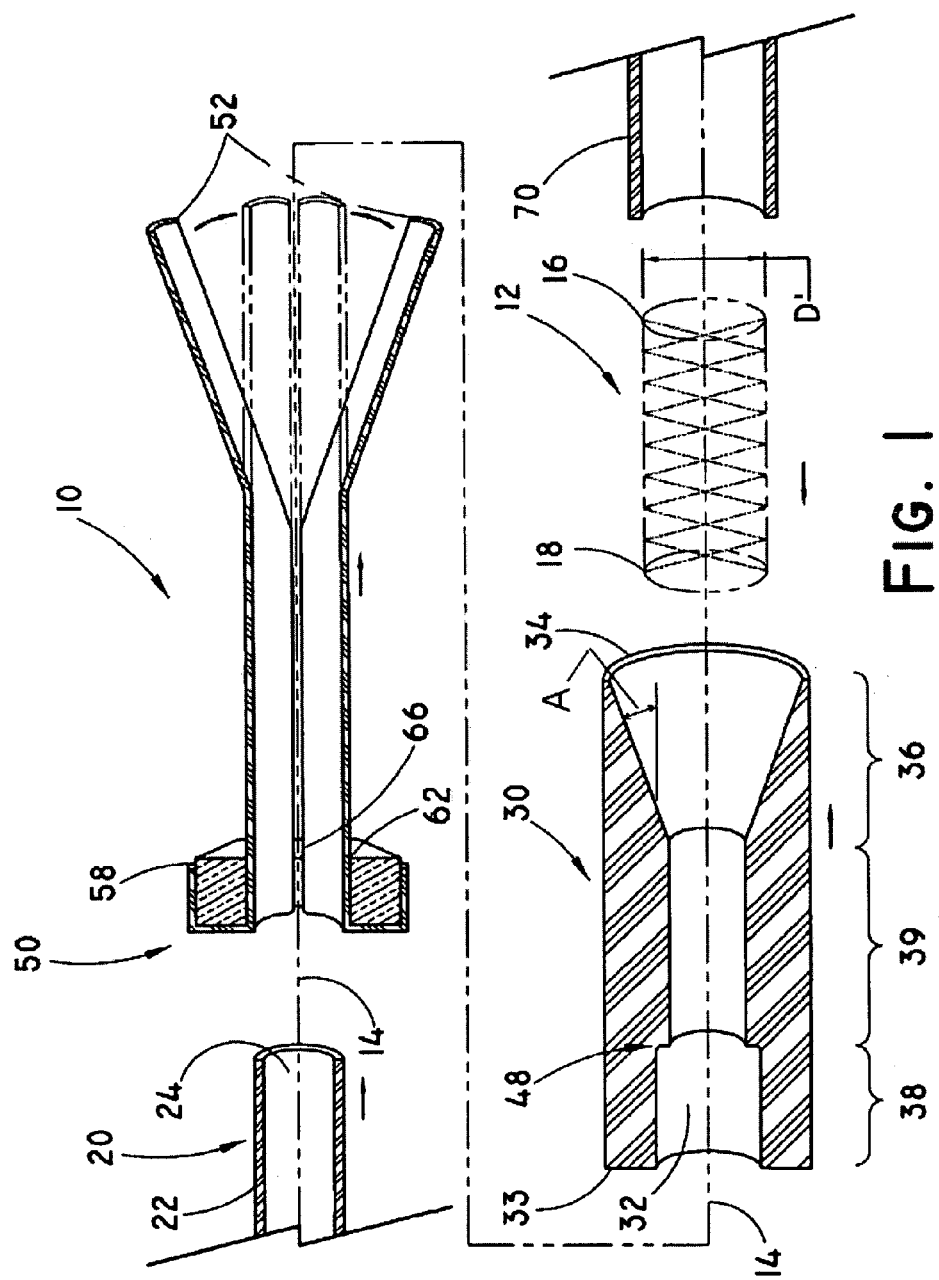
FIG. 1 is a side view of an exemplary system of the present invention for loading a tubular medical device into an introducer via a compressor and a split sleeve device.

FIG. 1 shows a system 10 for loading a tubular medical device 12 into an introducer 20 via a compressor 30 and a split sleeve device 50. The tubular medical device 12, such as a vascular stent or endprosthetic valve, preferably includes an abluminal surface and a luminal surface defining a cylindrical lumen about a longitudinal axis 14 extending longitudinally through the tubular medical device 12 from a first end 16 to a second end 18. In general, the tubular medical device 12 may comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube). Examples of tubular medical device 12 include endovascular, biliary, tracheal, gastrointestinal, urethral, ureteral, esophageal and coronary vascular stents or valves.

The tubular medical devices 12 may be, for example, balloon-expandable or self-expandable. The tubular medical device 12 may include a plurality of interconnected struts and bends in a plurality of longitudinally connected sinusoidal hoop members. The tubular medical device 12 may be radially movable between a compressed configuration (FIG. 4B) having a diameter, D, and a radially expanded, or un-compressed configuration, (FIG. 1) having a diameter, D'. In order to implant the tubular medical device 12 in a body vessel, the tubular medical device 12 can be reduced in diameter and introduced into the end of the introducer 20 by means of the compressor 30.

The tubular medical device 12 may have a valve that can be formed by attaching a means for regulating fluid flow, such as a valve leaflet, to any support member of the tubular medical device 12 described according to any of the embodiments. One or more valve devices can be implanted within the body vessel of a patient, especially a human, including for example in veins or arteries, to regulate fluid flow therein. The valve leaflet can be a single-leaflet type valve or a multiple-leaflet type valve. Preferably, each valve leaflet has a first edge and a second edge. The first edge can be disposed or attached on the middle region of the support member, while the second edge can extend between the first end and the second end of the support member and can be movable across the fluid flow path. Since the second edge can be moveable, the second edge can have an open position and a closed, or substantially closed, position to regulate fluid flow through fluid flow path of the tubular medical device 12.

In a vein, blood flow occurs in a pulsatile fashion, with surges in antegrade fluid flow occurring between intermittent retrograde fluid flow. The tubular medical device 12 having the valve preferably provides a one-way valve that permits intermittent antegrade blood flow while preventing the retrograde fluid flow in the opposite direction. Each valve leaflet is a flexible structure configured to moveably traverse the fluid flow path of the support frame, and configured to sealably engage the opposite wall of the body vessel The valve leaflet may be securely mounted to the support member by any suitable means, including but not limited to, adhesive, fasteners, and tissue welding using heat and/or pressure. Alternatively, the valve leaflet may be formed on the support member by any appropriate means, including but not limited to vapor deposition, spraying, electrostatic deposition, ultrasonic deposition, or dipping. In one embodiment, a sheet of material is cut to form a valve leaflet and the first edge of the leaflet is wrapped around portions of a support member and portions of the valve leaflet sealably connected together to fasten the valve leaflet around the support member.

The valve leaflet(s) can be formed of a remodelable material, such as small intestine submucosa (SIS) or other extracellular matrix (ECM) material. Remodelable materials, such as extracellular matrix (ECM) materials, can be used to provide a non-thrombogenic surface in an implantable prosthetic valve. The valve leaflets can be formed from a remodelable material such that, upon implantation, the remodelable material can become vascularized to form a permanently non-thrombogenic leaflet surface. Small intestinal submucosa (SIS) is a commercially available ECM material (Cook Biotech Inc., West Lafayette, Ind.) derived from a porcine source and processed to retain remodelability. The remodelable material can be isolated from biological tissue by a variety of methods. In general, a remodelable material such as ECM material can be obtained from a segment of intestine that is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until attached to the valve frame or implanted into the body.

The tubular medical device 12 may also include a separate anchor member attached to at least one of the first and second ends 16, 18, or therebetween, of the tubular medical device 12, or may be an integral anchor member formed from at least one of the first and second ends 16, 18. The term "anchor member" is used to denote any structure which can be used to help maintain the tubular medical device 12 in a desired relationship with a wall of the body vessel. For example, a hook or barb (not shown) could be formed from, or attached to, at least one of the first and second ends 16, 18 to serve as an anchor member. The anchor member may be at least partially insertible into the wall of the body vessel for a mechanical engagement therewith.

The tubular medical device 12 may further include a graft or layer of biocompatible material covering at least a portion of the tubular medical device 12. The graft material may be synthetic, such as polyester (e.g., Dacron®) (Invista, Wichita, Kans.), woven velour, polyurethane, PTFE, ePTFE, Gore-Tex® (W.L. Gore & Associates, Flagstaff, Ariz.), or heparin-coated fabric. Alternatively, the graft material may be a biological material such as bovine, equine, and/or porcine pericardium, peritoneal tissue, pleura, submucosal tissue, dura mater, an allograft, a homograft, a patient graft, or a cell-seeded tissue.

Moreover, a portion of the tubular medical device 12 may also be configured to include one or more mechanisms for the delivery of a therapeutic agent. Often the agent will be in the form of a coating or other layer (or layers) of material placed on a surface region of the tubular medical device 12 or the graft, which is adapted to be released at the treatment site of implantation, or areas adjacent thereto, of the tubular medical device 12.

Referring to FIGS. 1 and 2, the introducer 20 can be used for implanting the tubular medical device 12 into the body vessel. The introducer 20 can receive the tubular medical device 12 by means of the compressor 30. The introducer 20 can include an outer catheter 22, an inner catheter, and an inner shaft, all coaxially arranged. At the distal end of the inner shaft can be arranged a catheter tip, each forming a structural unit that can be inserted or retracted axially into or out of the inner catheter. The axially oriented lumen for the tubular medical device 12 to be inserted is provided in the lumen 24 of the outer catheter 22 between the cylindrical inner wall of the outer catheter 22 and the cylindrical outer wall of the free section of the inner shaft. The cross-sectional area of the lumen 24 of the outer catheter 22 is sized to accommodate a compressed tubular medical device 12. In the assembled state, the tubular medical device 12 is positioned with one end at the distal end face of the inner catheter and with the other end at the proximal rear face of the catheter tip.

The catheter tip may be provided with an axial bore opening into the recess of the catheter tip or into the lumen of the inner shaft. The introducer 20 may in addition be provided with a guide wire passing axially through the inner shaft and the catheter tip. The components of the introducer 20 are axially dimensioned such that in the assembled state a space corresponding approximately to the length of the compressed tubular medical device 12 is provided between the proximal end face of the catheter tip and the distal end face of the inner catheter. Once inserted into the body vessel, the introducer 20 travels through a series of vessels to reach a treatment site. As soon as the treatment site has been reached, the outer catheter 22 is retracted relative to the catheter tip, and as a result the tubular medical device 12 radially expands under the action of its own elastic restoring force to the predetermined outer diameter and is released. Once the tubular medical device 12 has been released, the introducer 20 can be removed from the body vessel. It is noted that the described introducer is merely one non-limiting embodiment of an introducer, and other types of introducers known in the art are to be included within the scope of the invention.

In FIG. 2, the compressor 30 includes a hollow housing having a passage 32 connecting a stent delivery end 33 and a stent receiving end 34. The passage 32 can have a funnel portion 36, an introducer opening 38, and a transitioning portion 39 positioned between the funnel portion 36 and the introducer opening 28.

The funnel portion 36 is shaped to radially compress the tubular medical device 12 before loading into the lumen 24 of the outer catheter 22 of the introducer 20. The funnel portion 36 is proximate the stent receiving end 34 and the introducer opening 38 is proximate the stent delivery end 33. The funnel portion 36 has a first end 40 with an opening having a cross-sectional area that is sized to receive the tubular medical device 12 in the expanded configuration. Starting from the first end 40 at the stent receiving end 34, the surface of passage 32 conically tapers in the direction of the introducer at an angle A to a second end 42 with a cross-sectional area less than the first end cross-sectional area, as shown in FIG. 2. The angle A can be approximately 5° to about 35° and preferably about 10°.

The transitioning portion 39 can be approximately equal to the length of the compressed tubular medical device 12, but can be shorter or longer. The transitioning portion is preferably a cylindrical chamber having a first end 43 adjacent the second end 42 of the funnel portion 36 and a second end 44 adjacent to the introducer opening 38. The first end 43 can have a cross-sectional area substantially the same as the cross-sectional area of the second end 44. The cross-sectional of the transitioning portion 39 can be slightly smaller than the cross-sectional area of the lumen 24 of the outer catheter 22 to ensure an easier transition from the funnel portion 36 to inside the lumen 24 of the outer catheter 22 of the introducer 20. The introducer opening 38 shaped and sized to receive the outer catheter 22 of the introducer 20 and sleeves 52 of the split sleeve device 50. The introducer opening 38 is preferably a cylindrical chamber having a first end 46 that is adjacent to the second end 44 of the transitioning portion 39 and a second end 47 proximate the stent delivering end 33. The cross-sectional area of the introducer opening 38 is generally larger than the cross-sectional area of the transitioning portion 39 or the second end 42 of the funnel portion 36. Because of the larger cross-sectional area, a seat 48 may be created at the juncture of the transitioning portion 39 and the introducer opening 38. The surface of the seat 48 can be generally perpendicular to the passage 32 or can be tapered, and can provide a stopping point for the introducer 20 when inserted into the introducer opening 38.

Referring to FIG. 3A, the split sleeve device 50 is provided to urge the tubular medical device 12 to a compressed configuration. The split sleeve device 50 includes at least one flexible sleeve 52 having a body 53 with a first end 54 and a second end 56. Preferably, the split sleeve device 50 has two sleeves 52a, 52b (FIG. 3B) or four sleeves 52a-d (FIG. 3C), but can be any number suitable to compress the tubular medical device 12. A discrete layer 57 of sleeves can be formed by two or more sleeves 52. The discrete layer 57 of sleeves can be overlapped by another discrete layer 59 of two or more sleeves 52, as shown in FIG. 3C, where one discrete layer 59 is disposed radially inward of the other discrete layer 57 of sleeves. The number and width of each sleeve 52 should be such that there can be overlap with adjacent sleeve edges of another discrete layer. It is preferable, however, that there be no collusion of sleeve edges of a given discrete layer. For example, the split sleeve device 50 can have (n) number of sleeves 52 and can have an angle B of $2\Pi/n$ between the center of the body 53 of each sleeve 52. The split sleeve device may also have (n') number of pair of sleeves 52 and can have an angle of $\Pi/n$ between the center of the body of each sleeve 52 of each pair.

The body 53 of the one or more sleeves 52 can be arcuate about the longitudinal axis 14 to form at least a portion of a tubular body. Each sleeve 52 is preferably made of clear, flexible polymer that will not stretch or deform plastically. For example, each sleeve 52 can be made of Kapton®, Nylon blends, polyethylene, Polyethylene terephthalate (PET) or reinforced materials or other materials having similar properties desirable for the functionality of the sleeve 52. One non-limiting method to make each sleeve 52 is to split or cut a thin-walled tubing into half, lengthwise to create strips. The tubing may have a wall thickness of 0.13 mm (0.005") and a diameter or cross-sectional area less than the inside cross-sectional area of the outer catheter 22 of the introducer 20. A portion 55 of the sleeve 52 can also flare radially outward at an angle C, as shown in FIG. 3A. It is preferable that the angle C be substantially the same as angle A of the funnel portion 36. For example, the angle C can be approximately 5° to about 35° and preferably about 10°. Optionally, the portion 55 of each sleeve 52 can be flared out at the angle C that is greater than the angle A.

According to FIG. 3A, the split sleeve device 50 includes a mounting device 58 that defines a hole 62 about the longitudinal axis 14. The hole 62 of the mounting device 58 is for receiving the sleeves 52 therethrough and is sized to receive the outer catheter 22 of the introducer 20. The sleeves 52 can be molded or formed integrally to the body of the mounting device 58, bonded by adhesives, soldered, welded or otherwise mechanically attached. In one embodiment, the mounting device 58 can be ring-like structure or a cylindrical body having a number (k) of planar surfaces 64 machined on the body of the mounting device 58. Optionally, the mounting device 58 can be polygon shaped with (k) number of planar surfaces 64 and can have an angle B of $2\Pi/k$ between the center of the body of each planar surface 64. The number (k) of planar surface 64 is preferably proportional to the number of sleeves 52. For example, the mounting device can have two planar surfaces 64a, 64b (FIG. 3B) or four planar surfaces 64a-d (FIG. 3C)

As shown in FIG. 3A, the first end 54 of the sleeves 52 can be coupled to the mounting device 58, and can conform to the hole 62 of the mounting device 58, extending outward from the hole 62 for wrapping around the mounting device 58 to attach the planar surface 64. The second end 56 can be flared radially outward at the angle C to receive the tubular medical device 12 therein. When coupled to the mounting device 58, each sleeve 52 can be separated by a longitudinal gap 66 or split with respect to the adjacent sleeve of the same discrete layer that allows radial flexibility to a degree that when radially collapsing compresses the tubular medical device 12. The sleeves 52 of one discrete layer 57 can overlap the sleeves of another discrete layer 59, where each discrete layer coves the longitudinal gap of the other discrete layer. The sleeves 52 can be inserted into each of the passage 32 of the compressor 30 and the mounting device 58, and translated axially along the longitudinal axis 14 to adjacent the stent delivery end 33. While in the passage 32, the sleeves 52 function as a liner, separating the passage walls of the compressor 30 from the tubular medical device 12. Some examples include sleeves 52 having a length greater than the length of the passage 32 to extend beyond the stent receiving end 34. The length of the sleeve 52 is suitable that, when collapsing the tubular medical device 12, the second end 56 of the sleeve 52 extends past the first end 16 of the tubular medical device 12. The body 53 of the sleeve in such examples can be flexible in order for the second end 56 of the sleeve 52 to extend outward from the passage 32 of the compressor 30 for wrapping around the exterior surfaces of the compressor 30, as shown in FIGS. 1 and 2.

Illustrated in FIG. 2 is an inserter 70 that can be provided to retain the tubular medical device 12 about the longitudinal axis 14 while the tubular medical device 12 collapses to the compressed configuration during loading. The inserter 70 can have a collapsible member 72 configured to retain the tubular medical device 12. One example of the collapsible member 72 includes a plurality of arms 74 extending radially outward from the inserter 70. Each arm 74 can have a stent engaging end 76 for contacting and retaining the tubular medical device 12 about the longitudinal axis 14 while the tubular medical device 12 is urged into the stent receiving end 34. Upon further travel into the funnel portion 36, the collapsible member 72 can be collapsible to a cross sectional area less than the cross sectional area of the outer catheter 22 of the introducer 20. This can allow the collapsible member 72 to be inserted into the lumen 24 of the outer catheter 24 of the introducer 20 when urging the tubular medical device 12 therein.

Referring to FIGS. 1, 4A and 4B, a method of loading the tubular medical device 12 into the introducer 20 is provided One step is to insert each sleeve 52 of the split sleeve device 50 through the passage 32 of the compressor 30. Because the portion 55 of the sleeve 52 is biased to radially expand, the portion 55 of the sleeve 52 will expand to contact the surface of the funnel portion 36. The second end 56 of each sleeve 52 may be wrapped around the stent receiving end 34 and the exterior surface of the compressor 30. The mounting device 58 of the split sleeve device 50 can be positioned adjacent to the stent delivery end 33 of the compressor 30. It is desirable that the mounting device 58 remain axially aligned with the compressor 30. The introducer 20 can be inserted through the hole 62 of the mounting device 58 and into the introducer opening 38 through the stent delivery end 33 of the compressor 30. The tubular medical device 12 can be inserted into the funnel portion 36 through the stent receiving end 34 of the compressor 30, where the second end 18 of the tubular medical device 12 contacts the wall of the funnel portion 36 and is positioned along the longitudinal axis 14 (FIG. 1).

The compressor 30 can be translated along the longitudinal axis 14 relative to the mounting device 58 (FIG. 4A). In one example, the mounting device 58 and/or inserter 70 is fixed relative to the compressor 30 that is translated away in a direction, represented by arrow 80, away from the mounting device 58. Here, the introducer 20 slidably engages the hole 62 of the mounting device 58 to remain contacting the introducer opening 38, preferably the seat 48, in order to be in a position to receive the tubular medical device 12. In another example (not shown), the compressor can be fixed, and the mounting device 58 and/or inserter 70 can be translated away in a direction away from the compressor. Here, the hole of the mounting device slidably engages the outside wall of the introducer, while the introducer remains contacting the introducer opening, preferably the seat, in order to be in a position to receive the tubular medical device. It may also be desirable for both the mounting device and the compressor to each move away from one another.

This translation of the compressor 30 relative to the mounting device 58 can urge the sleeves 52 to collapse, radially compressing the tubular medical device 12 into the compressed configuration. The cross-sectional area of the tubular medical device 12 in the compressed configuration can be substantially similar to the cross-sectional area of the second end 42 of the funnel portion 33. When the second end 56 of the sleeves is wrapped around the stent receiving end 34 and the exterior surface of the compressor 30 as illustrated in FIG. 2, the second end 56 will rotate in a direction, represented by arrow 82, radially inward. The tubular medical device 12 may then be urged into the transitioning portion 39 of the compressor 30, which may have a different cross-sectional area than that of the introducer opening 38. Upon further translation, the tubular medical device 12 can then be loaded into the lumen 24 of the outer catheter 22 of the introducer 20 (FIG. 4B).

The inserter 70 can be used to facilitate the process of loading the tubular medical device 12 into the introducer 20. The tubular medical device 12 can be inserted into the funnel portion 36 through the stent receiving end 34 of the compressor 30. The inserter 70 can engage and retain the tubular medical device 12 while the compressor 30 is translated along the longitudinal axis 14 relative to the mounting device 58. The inserter 70 may assist in urging the tubular medical device 12 into the transitioning portion 39 of the compressor 30. Upon further translation, the inserter 70 can load the tubular medical device 12 into the lumen 24 of the outer catheter 22 of the introducer 20. The loaded introducer 20 may then be withdrawn from the compressor 30 and the split sleeve device 50, and then introduced to the body vessel to deploy the tubular medical device 12 to a treatment site.

The compressor 30 and/or the split sleeve device 50 may be individually packaged and sterilized. Accordingly, the interventionalist can load the tubular medical device 12 at the bedside of a patient, which can be important when the tubular medical device 12 needs to be pre-treated, such as hydrated, or remain un-compressed up until the time of the procedure. Further, the compressor 30 and/or the split sleeve device 50 are preferably disposable after one-time use, or alternatively can be made of materials that can be cleaned, reset, sterilized and reused.

In accordance with the provisions of the patent statutes, the present invention has been described in what is considered to represent its preferred embodiment. However, it should be noted that the invention can be practiced otherwise than as specifically illustrated and described.

The invention claimed is:

1. A system for loading a self-expanding stent into an introducer having an outer tube defining a lumen, the system comprising:
   a compressor having a stent delivery end, a stent receiving end, and a passage about a longitudinal axis connecting the stent delivery end and the stent receiving end, the passage comprising a funnel portion proximate the stent receiving end and an introducer opening proximate the stent delivery end, the funnel portion at the stent receiving end being sized to receive an un-compressed stent, the introducer opening shaped and sized to receive the outer tube of said introducer; and
   a split sleeve device comprising at least one flexible sleeve having a first end and a second end, and a mounting device situated adjacent the stent delivery end of the compressor defining a hole about the longitudinal axis sized to surround the outer tube of the introducer, the first end of the split sleeve device being coupled to the mounting device, the second end of the split sleeve device extending through the compressor passage at least to the stent receiving end and being flared outward to surround the un-compressed stent;
   the mounting device with the first end of the split sleeve device being movable away from the compressor, the second end of the split sleeve device and the surrounded stent being drawn through the funnel portion to collapse the stent to a compressed configuration, the compressed stent being urged into the lumen of said introducer by the movement of the split sleeve device relative to the compressor and introducer.

2. The system of claim 1, wherein n is the number of sleeves and $2\pi/n$ is the angle between a center of the body of each sleeve, where a gap is defined between each sleeve, the gap being reduced when the sleeves collapse the stent.

3. The system of claim 1, wherein the body of the at least one sleeve is arcuate about the longitudinal axis to form at least a portion of a tubular body.

4. The system of claim 3, wherein the split sleeve device comprises a first discrete layer of two sleeves with a gap in between the sleeves and a second discrete layer of two sleeves with a gap between the sleeves disposed radially inward of the first discrete layer of sleeves, where the body of each sleeve of each discrete layer forms an angle of about $\pi$, and the first discrete layer is offset from the second discrete layer by an angle of about $\pi/2$, and where the first and second discrete layers of sleeves overlap one another.

5. The system of claim 1, wherein the mounting device comprises a cylindrical body having a number (k) of planar surfaces machined on the body of the mounting device proportional to the number of sleeves and $2\pi/k$ is the angle between a center of the body of each planar surface.

6. The system of claim 5, wherein the first end of the split sleeve device conforms to the hole of the mounting device, extending outward from the hole and attaching to a respective planar surface of the mounting device.

7. The system of claim 1, wherein the mounting device is fixed relative to the sliding implant compressor.

8. The system of claim 1, wherein the funnel portion of the compressor passage has a first end corresponding to the stent receiving end and a second end, the first end sized to receive the un-compressed stent and the second end having a cross-sectional area substantially the same or less than a cross-sectional area of the lumen of said introducer.

9. The system of claim 1, wherein the passage further comprises a transitioning portion interposed between the funnel portion and the introducer opening, the transitioning portion having a cross-sectional area substantially the same or less than a cross-sectional area of the lumen of said introducer.

10. The system of claim 1, wherein the compressor comprises a seat for said introducer within the introducer opening, the seat sized to prevent said introducer from advancing into the funnel portion.

11. The system of claim 1, further comprising an inserter having a collapsible member configured to retain said stent about the longitudinal axis while said stent collapses to the compressed configuration and is loaded into the lumen of said introducer.

12. The system of claim 11, wherein the collapsible member of the inserter comprises a plurality of arms extending radially outward from the inserter, each arm having a stent engaging end to retain said stent about the longitudinal axis while said stent collapses to the compressed configuration, the collapsible member being collapsible to a cross-sectional area less than a cross-sectional area of the introducer lumen, where the collapsible member is inserted into the lumen of said introducer when urging said stent into the lumen of said introducer.

13. A system for loading an endoprosthetic valve, being movable between an expanded configuration and a compressed configuration, into an introducer having an outer tube defining a lumen, the valve including a self expanding stent and at least one valve leaflet of remodelable material, the device comprising:
   a compressor having a stent delivery end, a stent receiving end, and a passage about a longitudinal axis connecting the stent delivery end and the stent receiving end, the passage comprising a funnel portion proximate the stent receiving end and an introducer opening proximate the stent delivery end, the funnel portion at the stent receiving end being sized to receive the valve in the expanded configuration, the introducer opening shaped and sized to receive the outer tube of said introducer;
   a split sleeve device comprising a first and a second discrete layer of flexible sleeves, the second discrete layer disposed radially inward with respect to the first discrete layer, each sleeve having a body of a given width including a first end and a second end and being separated with respect to the adjacent sleeve of the same discrete layer by a longitudinal gap, the sleeves of the first discrete layer being overlapped by the sleeves of the second discrete layer with each discrete layer covering the longitudinal gap of the other discrete layer, and a mounting device situated adjacent the stent delivery end of the compressor defining a hole about the longitudinal axis sized to surround the outer tube of the introducer and to receive each sleeve therethrough, the first end of each sleeve being coupled to the mounting device, the second end of each sleeve extending through the compressor passage at least to the stent receiving end, the second end of each sleeve being flared outward to surround the valve in the expanded configuration; and the compressor being movable relative to the mounting device with the first end of each sleeve, the second end of each sleeve and the surrounded valve being drawn through the funnel portion to collapse the valve to the compressed configuration, the compressed valve being urged into the lumen of said introducer by the movement of each sleeve relative to the compressor and introducer and the urging of the inserter.

14. The system of claim 13, wherein the body of each sleeve is arcuate about the longitudinal axis to form a tubular body.

15. The system of claim 13, wherein each sleeve conforms to the hole of the mounting device, the first end of each sleeve extending outward from the hole and attaching to a respective planar surface of the mounting device.

16. The system of claim 13, wherein the funnel portion of the sliding implant compressor passage has a first end corresponding to the stent receiving end and a second end, the first end sized to receive said valve in the expanded configuration and the second end having a cross-sectional area substantially the same or less than a cross-sectional area of the lumen of said introducer; and wherein the passage further comprises a transitioning portion interposed between the funnel portion and the introducer opening, the transitioning portion having a cross-sectional area substantially the same or less than the lumen cross-sectional area of said introducer.

17. The system of claim 13, further comprising an inserter having a collapsible member configured to retain said valve about the longitudinal axis while said valve collapses to the compressed configuration and is delivered to the lumen of said introducer, wherein the mounting device and the inserter are fixed relative to the movable compressor.

18. The system of claim 17, wherein the collapsible member of the inserter comprises a plurality of arms extending radially outward from the inserter, each arm having a stent engaging end to retain said valve about the longitudinal axis while said valve collapses to the compressed configuration, each arm being collapsible to a cross-sectional area less than a cross-sectional area of the introducer, where each arm is inserted into the lumen of said introducer when urging said valve into the lumen of said introducer.

19. A system for loading a self-expanding stent into an introducer having an outer tube defining a lumen, the system comprising:

a compressor having a stent delivery end, a stent receiving end, and a passage about a longitudinal axis connecting the stent delivery end and the stent receiving end, the passage comprising a funnel portion proximate the stent receiving end and an introducer opening proximate the stent delivery end, the funnel portion at the stent receiving end being sized to receive an un-compressed stent, the introducer opening shaped and sized to receive the outer tube of said introducer; and a split sleeve device comprising a plurality of flexible sleeves each having a first end and a second end, the split sleeve device having a plurality of gaps defined between the plurality of flexible sleeves and extending from the first end to the second end of each flexible sleeve of the plurality of flexible sleeves, and a mounting device situated adjacent the stent delivery end of the compressor defining a hole about the longitudinal axis sized to surround the outer tube of the introducer, the first end of each sleeve being coupled to the mounting device, the second end of each sleeve extending through the compressor passage at least to the stent receiving end and being flared outward to surround the un-compressed stent;

the mounting device with the first end of each sleeve being movable away from the compressor, the second end of each sleeve and the surrounded stent being drawn through the funnel portion to collapse the stent to a compressed configuration, the compressed stent being urged into the lumen of said introducer by the movement of each sleeve relative to the compressor and introducer.

20. The system of claim 19, further comprising an inserter having a collapsible member configured to retain said stent about the longitudinal axis while said stent collapses to the compressed configuration and is loaded into the lumen of said introducer.

* * * * *